United States Patent
Dallarosa

(10) Patent No.: US 9,371,957 B2
(45) Date of Patent: Jun. 21, 2016

(54) ARTICULATED ARM FOR DELIVERING A LASER BEAM

(75) Inventor: Joseph L. Dallarosa, Redwood City, CA (US)

(73) Assignee: RELIANT TECHNOLOGIES, LLC, Hayward, CA (US)

( * ) Notice: Subject to any disclaimer, the term of this patent is extended or adjusted under 35 U.S.C. 154(b) by 2118 days.

(21) Appl. No.: 11/566,092

(22) Filed: Dec. 1, 2006

(65) Prior Publication Data

US 2009/0230269 A1 Sep. 17, 2009

Related U.S. Application Data

(60) Provisional application No. 60/752,850, filed on Dec. 21, 2005.

(51) Int. Cl.

| F16M 11/12 | (2006.01) |
|---|---|
| A61B 18/20 | (2006.01) |
| F16M 11/10 | (2006.01) |
| F16M 11/20 | (2006.01) |
| A61C 9/00 | (2006.01) |
| A61C 1/00 | (2006.01) |

(52) U.S. Cl.
CPC ............ *F16M 11/12* (2013.01); *A61B 18/201* (2013.01); *A61C 9/0053* (2013.01); *F16M 11/10* (2013.01); *F16M 11/2035* (2013.01); *A61C 1/0046* (2013.01)

(58) Field of Classification Search
USPC .......................................................... 606/19
See application file for complete search history.

(56) References Cited

U.S. PATENT DOCUMENTS

| 4,122,853 | A | | 10/1978 | Smith |
| 4,539,462 | A | * | 9/1985 | Plankenhorn ............ 219/121.79 |
| 4,575,610 | A | * | 3/1986 | Gavin ......................... 219/121.6 |
| 4,623,229 | A | * | 11/1986 | Galan .......................... 359/845 |
| 4,659,916 | A | | 4/1987 | Muller et al. |
| 4,661,681 | A | * | 4/1987 | Bannister .................. 219/121.78 |
| 4,760,583 | A | * | 7/1988 | Sasnett et al. .................. 372/109 |
| 4,917,083 | A | | 4/1990 | Harrington et al. |
| 5,342,352 | A | * | 8/1994 | Franken et al. ..................... 606/9 |
| 5,413,555 | A | | 5/1995 | McMahan |
| 5,484,982 | A | * | 1/1996 | Nihei et al. .............. 219/121.79 |
| 5,820,623 | A | * | 10/1998 | Ng ..................................... 606/1 |
| 6,236,906 | B1 | | 5/2001 | Muller |
| 6,519,860 | B1 | | 2/2003 | Bieg et al. |
| 6,840,934 | B2 | | 1/2005 | Enomoto |
| 2003/0028181 | A1 | | 2/2003 | Enomoto |
| 2005/0285928 | A1 | | 12/2005 | Broome et al. |

FOREIGN PATENT DOCUMENTS

DE 10333456 A1 2/2005

OTHER PUBLICATIONS

European Patent Office, search report issued in related European Application No. 06838951.9 dated Dec. 23, 2009.

\* cited by examiner

*Primary Examiner* — Brian Jennison
(74) *Attorney, Agent, or Firm* — Thompson Hine LLP; Toan Vo

(57) ABSTRACT

A laser assembly includes a laser and an articulated arm having a plurality of couplers arranged to receive a laser-beam from the laser. The assembly is mounted on a support structure, and is rotatable on the support structure in two axes perpendicular to each other. Six degrees of freedom of motion of the end of the articulated arm can be accomplished with one less coupler in the arm than would be necessary without rotation of the assembly on the support structure.

6 Claims, 4 Drawing Sheets

ARTICULATED ARM FOR DELIVERING A LASER BEAM

CROSS-REFERENCE TO RELATED APPLICATIONS

This application claims the benefit of U.S. Provisional Application No. 60/752,850, filed on Dec. 21, 2005 entitled "Articulated Arm for Delivering a Laser Beam," the entire disclosure of which is hereby incorporated by reference herein, including any appendices or attachments thereof, in its entirety for all purposes

TECHNICAL FIELD OF THE INVENTION

The present invention relates in general to apparatus or devices for delivery of a laser beam from a laser to a workpiece, handpiece or apparatus remote from the laser. The invention relates in particular to delivery of the laser beam via an articulated arm.

DISCUSSION OF BACKGROUND ART

In many laser applications, it is necessary to deliver a beam of radiation from the laser to a device remote from the laser that must have as many as six degrees of freedom of movement in space. Such applications include, in particular delivery, of a laser beam to a handpiece or applicator for applying the laser beam in a medical or dental treatment. A handpiece or applicator may include focusing optics for the beam or a scanning arrangement for scanning the beam over a treatment area. A common and convenient delivery arrangement for laser radiation having a wavelength in the visible or near infrared region of the electromagnetic spectrum is to transport the radiation (beam) from the laser to the handpiece via an optical fiber or a bundle of optical fibers.

Transmission via optical fibers is practically limited to radiation having a wavelength less than about 2600 nanometers (nm). At wavelengths longer than this, delivery is usually effected via what is generally referred to by practitioners of the art as an articulated arm. An articulated arm comprises a plurality of tubes joined one to another via one-axis or two axis rotatable joints or couplers. Internal mirrors in the couplers steer a beam through the arm from one tube to another, and along the length of the tubes.

FIG. 1 schematically illustrates one example 10 of a commercially available articulated arm supplied by LASER MECHANISMS™, INC. Farmington Hills, Mich. Arm 10 includes a launch housing 12 having a mounting plate 14, fixedly attachable to a laser (not shown). The laser beam enters the housing via an aperture 16 in plate 14, and is directed by a mirror LM into a first tube 18 of the arm. The beam is directed out of tube 18 by first mirror M1 housed in a joint or coupler 22 including mirrors M1 and M2 (not visible in the FIG. 1). Mirrors M1 and M2 direct the beam into and along a second tube 20. Coupler 22 between tubes 18 and 20 permits pivoting or rotation of the coupler and mirror M1 about the longitudinal axis of tube 18 as indicated by arrows R1, and permits pivoting of tube 20 about an axis perpendicular to the longitudinal axis of tube 20 (and tube 18) as indicated by arrows R2. Tube 20 is supported by an elongated support member 24 having a right angled bracket 26 thereon, to which is attached a counter weight 28.

Tube 20 is attached to a tube 30 by another coupler 32 including mirrors M3 and M4. Coupler 32 is rotatable about the longitudinal axis of tube 20 as indicated by arrows R3, and permits pivoting of tube 30 about an axis perpendicular to the longitudinal axis of tube 30 as indicated by arrows R4. The beam traveling along tube 20 is reflected via mirrors M3 and M4 into and along tube 30. A coupler 34, at an end of tube 30 includes a mirror M5 and a mirror M6 and is pivotable about the longitudinal axis of tube 30 as indicated by arrows R5 and about an axis perpendicular to the longitudinal axis of the tube 30 as indicated by arrows R6. Mirrors M5 and M6 in coupler 34 direct the beam from tube 30 through two right-angle bends in a direction perpendicular to the longitudinal axis of tube 30. A final coupler 36 includes a mirror M7 and is pivotable about the axis of the section emerging from coupler 36 as indicated by arrows R7. Coupler 36 has a flange 38 thereon from which the laser beam is delivered, and to which can be attached a handpiece or the like (not shown in FIG. 1) for focusing, shaping, dividing or scanning the beam. Such a handpiece, being attached to flange 38, would be pivotable as indicated by arrows R7.

In this type of arm, the two long arms 18 and 20 and rotations R1, R2 and R4 are primarily responsible for selection the position of the output end of the arm in a three dimensional working space or volume around the launch unit, definable in terms of X, Y, Z Cartesian axes. Three degrees of freedom of movement along these axes determine the position of the end of the arm in the working volume. The remaining rotations R3, R5, R6 and R7, cooperative with the other rotations, provide three additional degrees of freedom, i.e., rotation (pivoting) about the X-axis, pivoting about the Y-axis, and pivoting about the Z-axis.

Each mirror in an articulated arm is a source of energy loss in a beam as the mirrors are never exactly 100 percent reflective for the wavelength of the laser radiation. Even if each mirror has a reflectivity of 99%, the total energy loss from absorption in a seven mirror arm will be 7%. Further, no matter how well engineered coupler of the articulated arm may be, the couplers will never be completely free of play and accumulation of play at all of the joints can result in movement-sensitive changes in direction (pointing) of the beam as the beam leaves the articulated arm. Because of a requirement for freedom and smoothness of pivoting together with minimizing of free play in rotatable joints, the couplers are expensive and contribute to most of the cost of an articulated arm. The cost of such an arm is essentially proportional to the number of couplers therein. Clearly, it would be advantageous if the number of mirrors and couplers in an articulated arm could be reduced to reduce energy losses and beam pointing variations, and reduce the cost of the arm without giving up degrees of freedom of movement of a handpiece or the like attached to the arm. A typical handpiece at the end of the arm may require the laser beam to maintain an input tolerance of 10 to 100 micrometers (μm). For a one-meter-long arm, this means that the combined angular tolerance for all couplers combined must be less than 10 to 100 microradians.

SUMMARY OF THE INVENTION

In one aspect, apparatus in accordance with the present invention comprises a support structure, and an assembly including a laser and an articulated arm arranged to receive a laser-beam generated by the laser. The assembly is mounted on the support structure and pivotable on the support structure in at least two axes transverse to each other.

In one preferred embodiment of the inventive apparatus, the support structure includes a base, a bearing sleeve, and a vertical support post. The vertical support post is inserted into, and free to rotate in the bearing sleeve, providing for pivoting of the assembly about one-axis. The assembly is pivotably supported on a transverse pivot post extending outward from the vertical support post, providing for rotation of the assembly about a second axis perpendicular to the first axis. The two-axes rotatability or pivotability of the assembly on the support structure can provide the above described six degrees of freedom of rotation using an articulated arm with one less coupler than would be necessary in the prior-art laser and articulated arm arrangement discussed above.

DETAILED DESCRIPTION OF THE INVENTION

Figure 2:
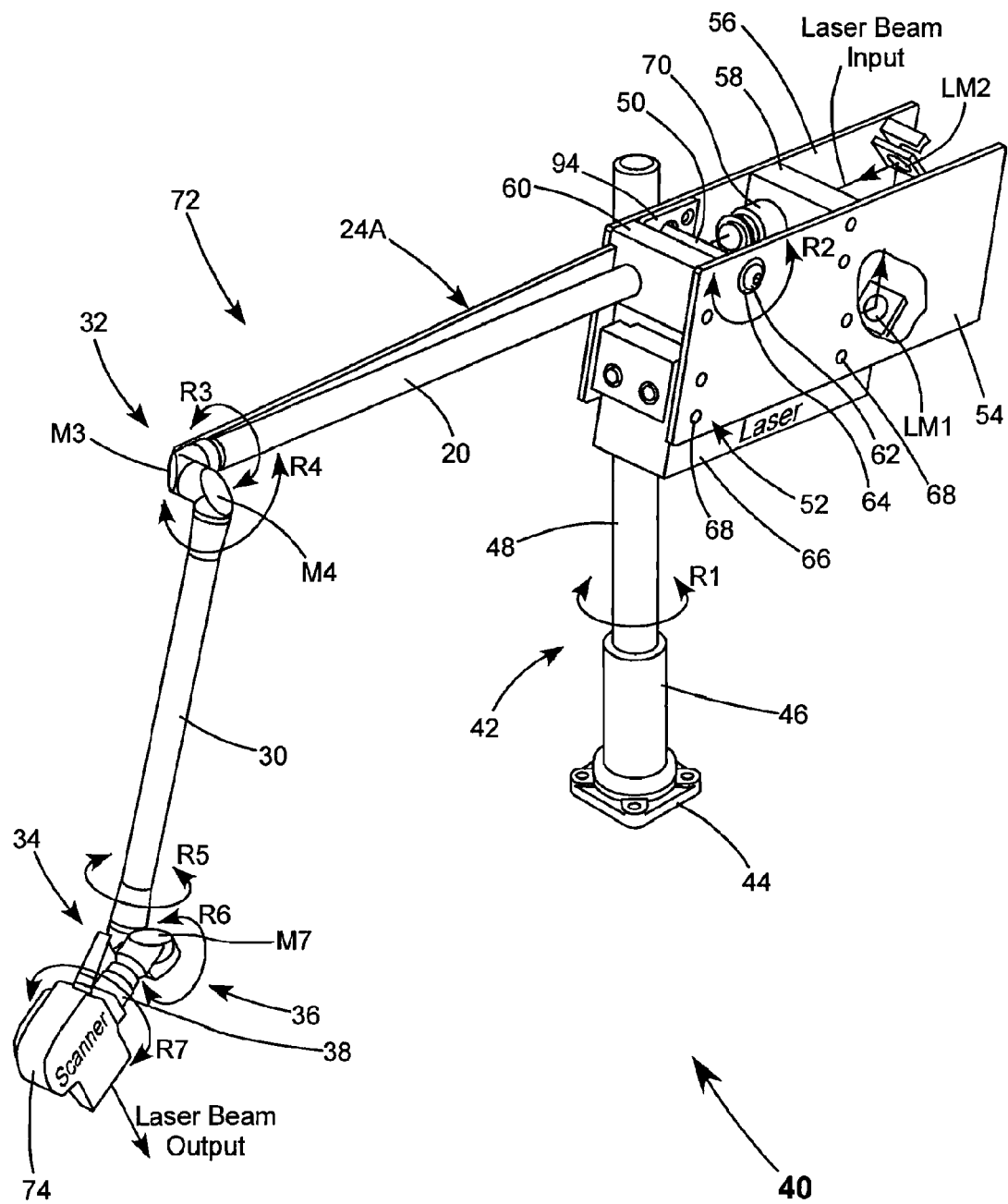
FIG. 2 schematically illustrates one embodiment of apparatus in accordance with the present invention wherein a laser is mounted in a frame supported on a support structure with the frame being pivotable about the support structure, via two different bearings, in two axes transverse to each other, and wherein an articulated arm is attached to the frame and fixedly aligned with the laser for receiving a beam from the laser and directing the laser beam to an infinitely variable location, with the frame-pivoting and the articulated arm together providing six degrees of freedom of movement, within a working volume, and wherein the articulation is similar to the articulated arm of FIG. 1, but has one less tube and one less coupler.

Referring again to the drawings, wherein like components are designated by like reference numerals, FIG. 2 schematically illustrates a preferred embodiment 40 of apparatus in accordance with the present invention. Apparatus 40 includes a support structure 42 including a base 44 to which is attached a cylindrical bearing socket or sleeve 46. A vertical support post 48 is inserted into sleeve 46 and is pivotable or rotatable about the longitudinal axis of the sleeve as indicated by arrows R1. The terms pivotable and rotatable are used interchangeably herein in recognizing that in most practical uses of the inventive apparatus it will not be necessary to rotate any joint or coupler through more the 360 degrees.

Continuing with reference to FIG. 2, support axle or pivot post 50 is attached to support post 48 and extends transversely (here, perpendicularly) therefrom. A frame 52 includes parallel sideplates 54 and 56, and spacing or support blocks 58 and 60. Frame 52 is pivotably suspended on pivot post 50 of support structure 42 and retained on the post by a screw 62 and washer 64. A laser 66 is attached, here via screws 68, to the side plates of frame 52. Also attached to the side plates are launch mirrors LM1 and LM2. A telescope 70 is mounted on spacing block 58.

Also attached to frame 52 is an articulated arm 72. Articulated arm 72 is configured similar to prior-art articulated arm 10 of FIG. 1 but does not include launch housing 12, launch mirror LM, first tube 18, coupler 22, with mirrors M1 and M2 therein, and counterweight 28 of that arm. All components common to arm 10 and arm 12 are designated with like reference numerals, with the exception of elongated support member 24 of articulated arm 10, which is replaced in arm 72 of FIG. 2 by a somewhat similar elongated member 24A.

Elongated member 24A has a bracket 94 at one end thereof and is attached to sidewall 56 of frame 52 via that bracket. The first long tube 20 of articulated arm 72 is attached at a proximal end thereof, via an aperture (not expressly designated) in support block 60, to frame 52. Tube 20 is supported at a distal end thereof (to which is attached coupler 32) by elongated member 24A.

Laser 52 is arranged to deliver a beam, initially in a direction away from the proximal end of tube 20. The beam from the laser 66 is redirected by launch mirrors LM1 and LM2 through beam-conditioner telescope 70. Telescope 70 is an optional component that is included in situations where beam shaping is required prior to launching a beam into articulated arm 72. Elongated member 24A and support block 60 maintain tube 20 in a fixed alignment with the beam path leaving mirror M2, such that the beam travels along tube 20 to coupler 32, and through remaining components comprising mirrors M3, M4, M5, M6, and M7, of the articulated arm 72 as described above with reference to arm 10 of FIG. 1. In FIG. 2, a scanning handpiece 74 is attached to flange 38 of the articulated arm.

Those skilled in the art will recognize that one reason for what might be described as a "reverse" mounting of the laser 66 in frame 52 is that the two mirrors LM1 and LM2 allow alignment of the laser beam to provide more accurate injection of the laser beam into the articulated arm 72. In an alternate configuration, the laser could be mounted such that the output was pointed in the direction of tube 20. In that alternate configuration, LM1 and LM2 would not be necessary.

Figure 1:
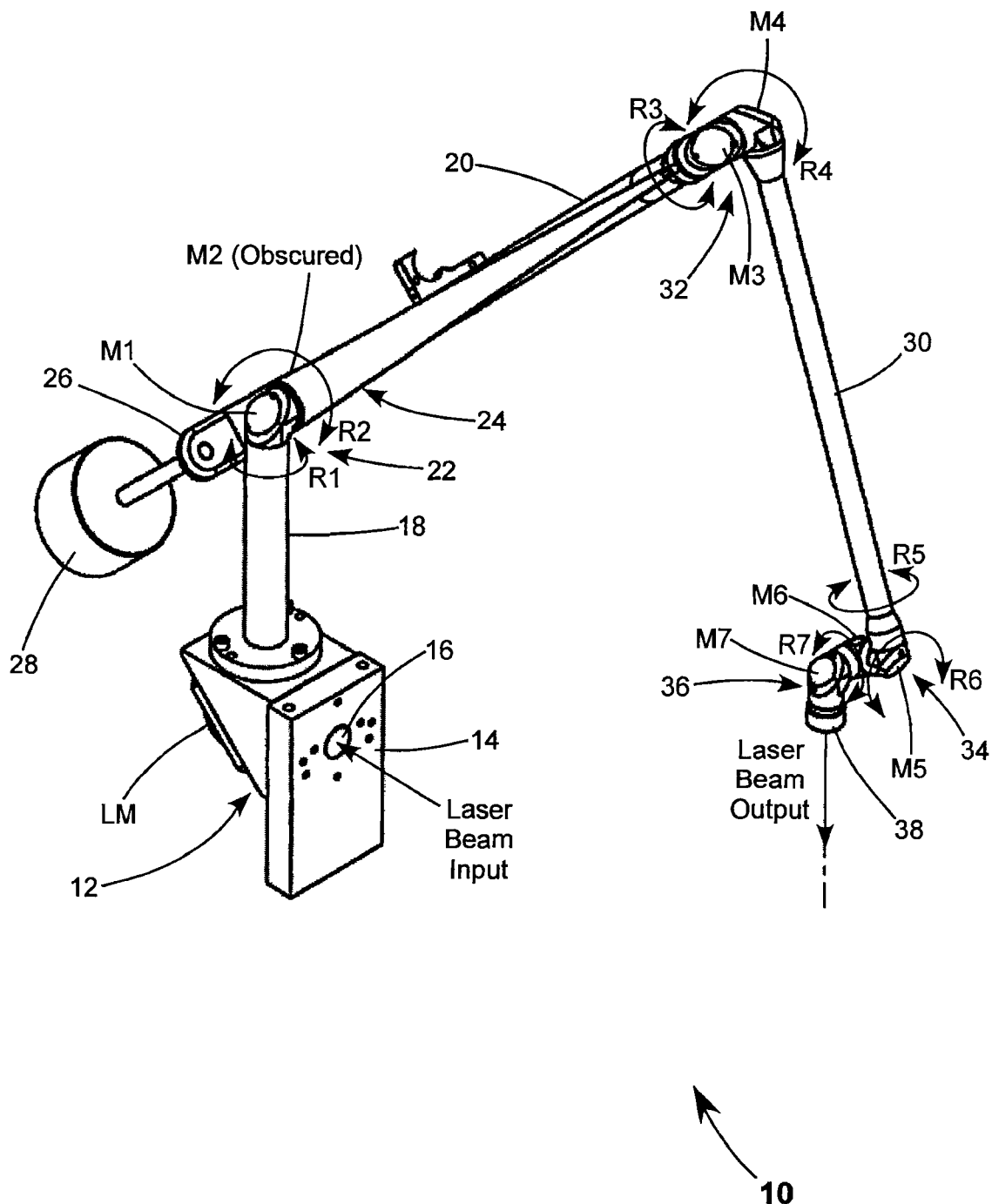
FIG. 1 schematically illustrates one example of a prior-art articulated arm for receiving a laser beam input and directing the laser beam to an infinitely variable location with six degrees of freedom of movement within a working volume, the articulated arm including a plurality of tubes connected by couplers that allow pivoting of one tube with respect to another about two axes, one transverse to the other.

In apparatus 40, the laser and the articulated arm 72, being fixedly attached to frame 52, are pivotable or rotatable in space about two axes transverse to each other, as indicated in FIG. 2 by arrows R1 and R2. In the arrangement of FIG. 1 which anticipates a fixedly mounted laser, rotations R1 and R2 are supplied by coupler 22. Accordingly the apparatus of FIG. 2 with an articulated arm having three pivotable couplers provides the same degrees of freedom of motion for a handpiece attached to the arm as are provided by prior-art articulated arm 10 which requires four pivotable couplers to provide those degrees of freedom.

Figure 3:
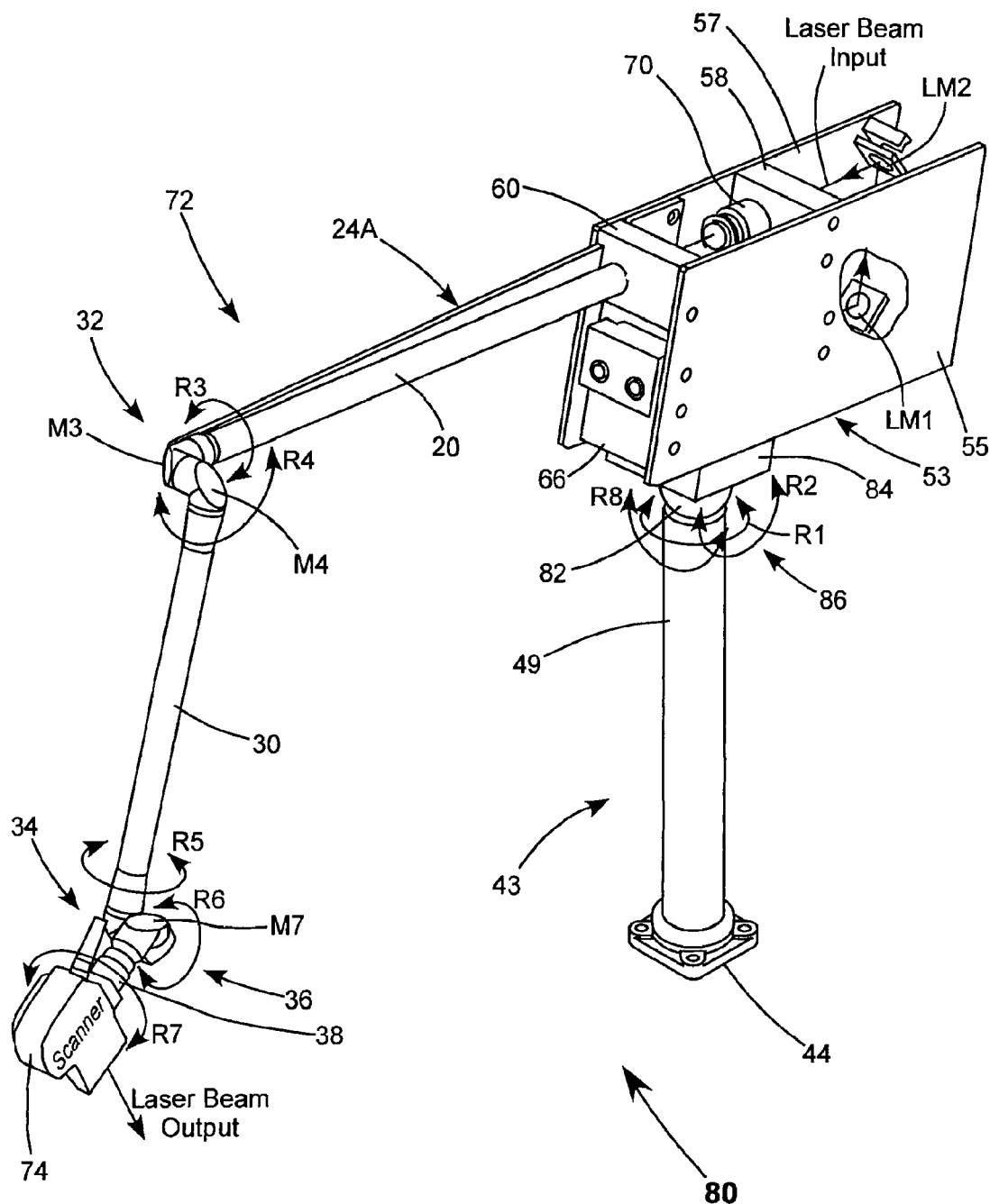
FIG. 3 schematically illustrates another of embodiment of apparatus in accordance with the present invention, similar to the apparatus of FIG. 2, but wherein the two separate bearings of the support structure are replaced by a ball and socket joint connecting the laser frame to the support structure.

FIG. 3 schematically illustrates another preferred embodiment 80 of laser apparatus in accordance with the present invention. Apparatus 80 is similar to apparatus 40 of FIG. 2 with exceptions as follows. Support structure 42 of apparatus 30 is replaced in apparatus 80 by a support structure 43. Support structure 43 includes a base 44 and a vertical support post 49 to which is attached ball member 82. Ball member 82 inserted in a mating socket (not shown) in a bearing block 84. The ball member 82 and the bearing block 84, together, provide a ball-and-socket joint 86. Frame 52 of apparatus 30 is replaced in apparatus 80 by a frame 53. Frame 53 is similar to frame 52 but side plates 54 and 56 of frame 52 are replaced by extended side plates 55 and 57, which allow bearing block 84 of ball and socket joint 86 to be attached to frame 53. Ball and socket joint 86 permits rotation of the frame 53 (with the laser 66 and articulated arm 72 attached thereto) about axes transverse (here, perpendicular) to each other as indicated by arrows R1 and R2. These rotations are similar to rotations R1 and R2 in apparatus 30 which are enabled by bearing socket 46 and pivot post 50 of support structure 42. The ball and socket joint of FIG. 3, however provides an additional rotation indicated in FIG. 3 by arrows R8, transverse to both rotations R1 and R2.

Those skilled in the art will recognize that a ball and socket joint suitable for apparatus 80 would cost significantly more than the cost of the simple pivot arrangements in support structure of apparatus 30, and the additional rotation provided may be superfluous when using an articulated arm with three couplers. Alternatively, the rotation R8 could be used to replace the rotation R3 if full 360° rotation at R3 were not desired and the and the angles required for R3 could be adequately replaced by R8. With a joint of this or a similar type, the bearing block 84 of the joint could be attached to frame 53 in a manner such that the position of the block on the frame could be adjusted for finely balancing the apparatus on the support structure.

Figure 4:
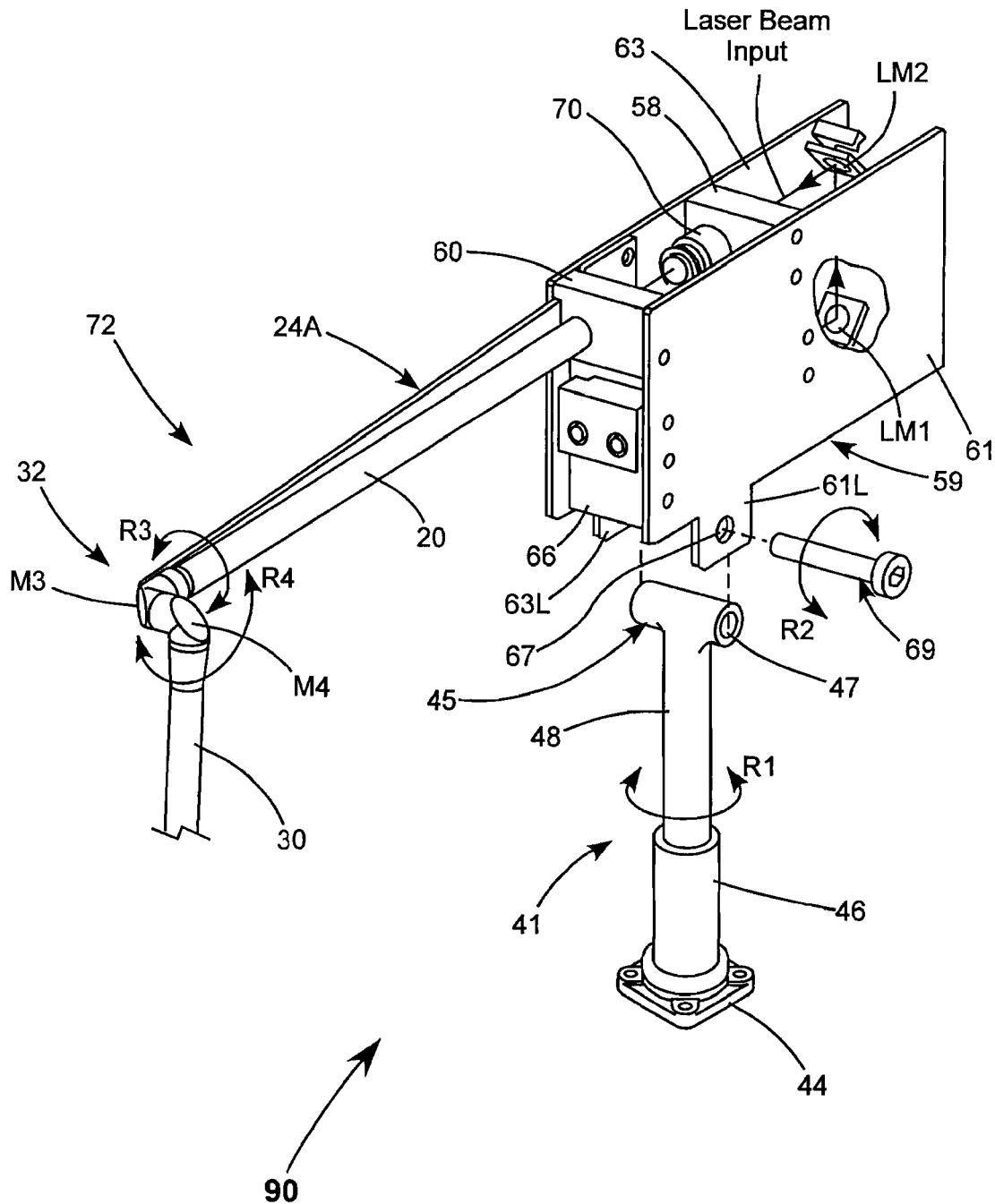
FIG. 4 is an exploded view schematically illustrating yet another of embodiment of apparatus in accordance with the present invention, similar to the apparatus of FIG. 2 but with an alternative implementation of the two separate bearings.

FIG. 4 is an exploded view schematically illustrating yet another of embodiment 90 of apparatus in accordance with the present invention. Apparatus 90 is similar to apparatus of FIG. 2 with exceptions as follows. Support structure 42 of apparatus 30 is replaced in apparatus 80 by a support structure 41. Support structure 41 includes a base 44, a bearing sleeve 46 and a vertical support post 48 which is rotatable in bearing sleeve 46 as indicated by arrows R1. A cylindrical bearing sleeve 45 having an aperture 47 extending therethrough is welded to post 48 with the longitudinal axis of bearing sleeve 45 being transverse (here, perpendicular) to the longitudinal axis of the post.

Frame 52 of apparatus 40 is replaced in apparatus 90 by a frame 59. Frame 59 is similar to frame 52, but side plates 54 and 56 of frame 52 are replaced by extended side plates 61 and 63, having lug portions 61L and 63L, respectively, extending downward. When apparatus 90 is assembled, bearing sleeve 45 of support structure 41 fits between lug portions 61L and 63L of the side plates of frame 59, and a pivot pin 69 is inserted through an aperture 67 in lug portion 61L of plate 61, through aperture 47 in bearing sleeve 45 of support structure 41, and through an aperture (not visible) in lug portion 63L of side plate 63 of frame 59. Pin 69 is retained in frame 59 by a nut (also not shown).

In above-described embodiments of the inventive apparatus, an articulated arm including three rotatable couplers is depicted. Those skilled in the art will recognize that the inventive two-axis or three-axis pivotable mounting of the laser and articulated arm on a support structure is useful with articulated arms having less than the 3 couplers of arm 72. The three-coupler articulated arm 72 of apparatus 40, apparatus 80, and apparatus 90 is useful in medical applications where a handpiece or the like, attached to the arm, must follow rising and falling contours, with varying slope, in any direction over a part of the human body being treated by radiation from the laser. In other applications such as laser machining, cutting, or drilling, on a plane substrate, however, an arm having only two couplers or even only one coupler may be sufficient, given the inventive rotations of the laser and articulated arm on the support structure. Accordingly, the present invention should not be construed as limited to the particular, three-coupler articulated arm 72.

In summary the present invention is described above in terms of a preferred and other embodiments. The invention is not limited, however, to the embodiments described and depicted. Rather, the invention is limited only by the claims appended hereto.

What is claimed is:
1. A laser apparatus comprising:
   a frame including a first side plate and a second side plate in a spaced parallel arrangement relative to the first side plate;
   a laser attached to said first and second side plates of said frame, said laser configured to generate a laser beam;
   an articulated arm attached to said frame, said articulated arm arranged relative to said laser to receive the laser beam; and
   a support structure including a base, a first support post extending vertically from said base, and a second support post extending horizontally between said first and second side plates,
   wherein said frame, said laser, and said articulated arm are attached as an assembly to said second support post for rotation relative to said first support post about a first axis of rotation, and said first support post is rotatable relative to said base about a second axis of rotation perpendicular to the first axis of rotation.
2. The apparatus of claim 1, wherein said articulated arm includes an interconnected plurality of tubular members and an inlet aperture to said plurality of tubular members, and further comprising:
   at least one mirror attached to said first and second side plates of said frame and arranged between said laser and said inlet aperture to direct the laser beam generated by said laser into said articulated arm.
3. The apparatus of claim 2, further comprising:
   first and second mirrors attached to said first and second side plates of said frame and arranged between said laser and said inlet aperture, said first and second mirrors configured to turn the laser beam generated by said laser though an angle of about 180 degrees before the laser beam is received by said articulated arm.
4. The apparatus of claim 3 further comprising:
   a telescope mounted to said side plates of said frame and located between said second mirror and said inlet aperture to said articulated arm for shaping the laser beam before the laser beam is received by said articulated arm.
5. The apparatus of claim 1, wherein said articulated arm includes a first tubular member, a second tubular member, and a coupler connecting said first and second tubular members such that said second tubular member is to rotatable relative to said first tubular member about two mutually perpendicular axes, said first tubular member being at a proximal end of said articulated arm and held in a fixed relationship with the laser and arranged to receive the laser beam, and said coupler providing that said second tubular member is rotatable on said first tubular member in two axes perpendicular to each other.
6. The apparatus of claim 5, further comprising:
   a handpiece attached to a distal end of said articulated arm and arranged to apply the laser beam to a surface to be treated by the laser beam.

* * * * *